United States Patent [19]

Chen

[11] Patent Number: 5,205,826
[45] Date of Patent: Apr. 27, 1993

[54] AUTOMATICALLY BLOCKED SAFETY SYRINGE

[76] Inventor: Long-Hsiung Chen, c/o Hung Hsing Patent Service Center, P.O. Box 55-1670, Taipei (10477), Taiwan

[21] Appl. No.: 983,144

[22] Filed: Nov. 30, 1992

[51] Int. Cl.$^5$ .............................................. A61M 5/00
[52] U.S. Cl. ...................................... 604/110; 604/195
[58] Field of Search ............... 604/110, 187, 195, 220, 604/228, 218

[56] References Cited

U.S. PATENT DOCUMENTS 4,804,370 2/1989 Haber et al. .......................... 604/110
5,104,378 4/1992 Haber et al. .......................... 604/110

*Primary Examiner*—John D. Yasko

[57] ABSTRACT

A syringe includes a hollow needle preliminarily held in a rigid blocking disk embedded in a rear disk socket perpendicularly formed in a flexible plug inserted in a front portion of the syringe for injection use having a needle head portion formed on a rear portion of the needle, and a plunger slidably held in the syringe for boosting a liquid medicine in the syringe to be injected into a patient through the hollow needle having a needle-head socket recessed in the plunger to be engageable with the needle-head socket for pushing the needle head portion of the needle frontwardly to drive the rigid blocking disk frontwardly to engage the blocking disk into a front disk socket which is normally inclinedly formed in the flexible plug and will be operatively perpendicularly biased in the plug when approximately exhausting the liquid in the syringe and finishing the injection, whereby upon a retraction of the plunger and the needle with the needle head portion received in and coupled to the plunger into the syringe to disengage the needle from the rigid disk, the flexible plug will restore the front socket and the rigid disk embedded in the front socket to be inclinedly positioned in the plug, thereby blocking an outward protruding of the needle retracted in the syringe for preventing its injury or infectious contamination to the surroundings.

8 Claims, 5 Drawing Sheets

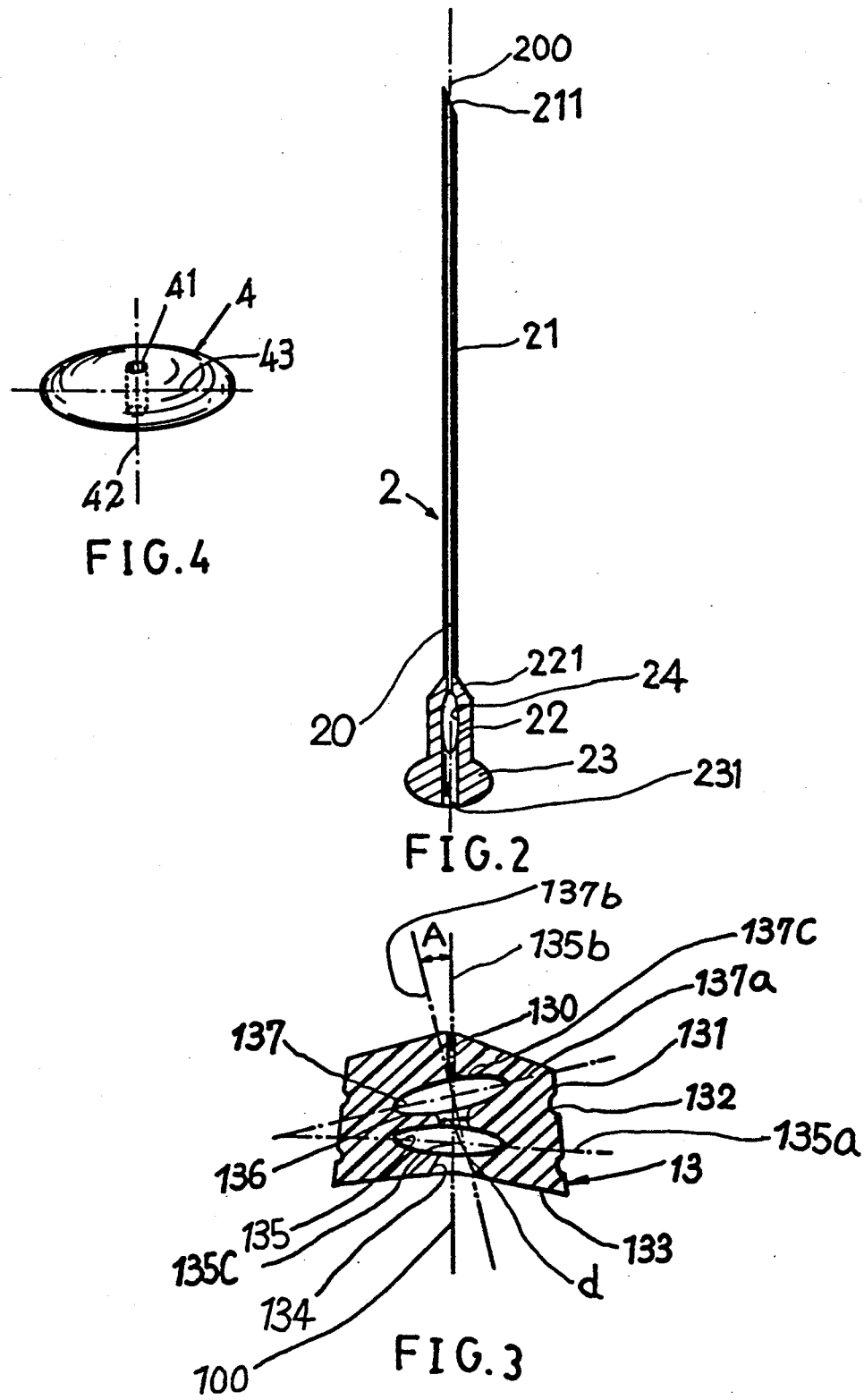

AUTOMATICALLY BLOCKED SAFETY SYRINGE

BACKGROUND OF THE INVENTION

A conventional syringe after being used for medical injection purpose will be treated for waste disposal. If the injection needle mounted on the syringe is protruded outwardly, it may cause infectious contamination or pollution, hazardous to environmental protection and human health. Even some improvements had been made to automatically retract the injection needle into the syringe body to prevent injury or infectious contamination to someone, the retracted needle as spring tensioned may still be inadvertently protruded outwardly by an external force or protruded downwardly when pendently held or when disposed in a garbage yard for an accidentally protruding of the needle to cause injury to the others.

SUMMARY OF THE INVENTION

The object of the present invention is to provide a safety syringe including a hollow needle preliminarily held in a rigid blocking disk embedded in a rear disk socket perpendicularly formed in a flexible plug inserted in a front portion of the syringe for injection use having a needle head portion formed on a rear portion of the needle, and a plunger slidably held in the syringe for boosting a liquid medicine in the syringe to be injected into a patient through the hollow needle having a needle-head socket recessed in the plunger to be engageable with the needle-head socket for pushing the needle head portion of the needle frontwardly to drive the rigid blocking disk frontwardly to engage the blocking disk into; a front disk socket which is normally inclinedly formed in the flexible plug and will be operatively perpendicularly biased in the plug when approximately exhausting the liquid in the syringe and finishing the injection, whereby upon a retraction of the plunger and the needle with the needle head portion received in and coupled to the plunger into the syringe to disengage the needle from the rigid disk, the flexible plug will restore the front socket and the rigid disk embedded in the front socket to be inclinedly positioned in the plug, thereby blocking an outward protruding of the needle retracted in the syringe for preventing its injury or infectious contamination to the surroundings.

BRIEF DESCRIPTION OF THE DRAWINGS

FIG. 2 is a sectional drawing of a hollow needle of the present invention.

FIG. 3 is a sectional drawing of a flexible plug of the present invention.

FIG. 4 is an illustration of a rigid blocking member of the present invention.

DETAILED DESCRIPTION

Figure 1:
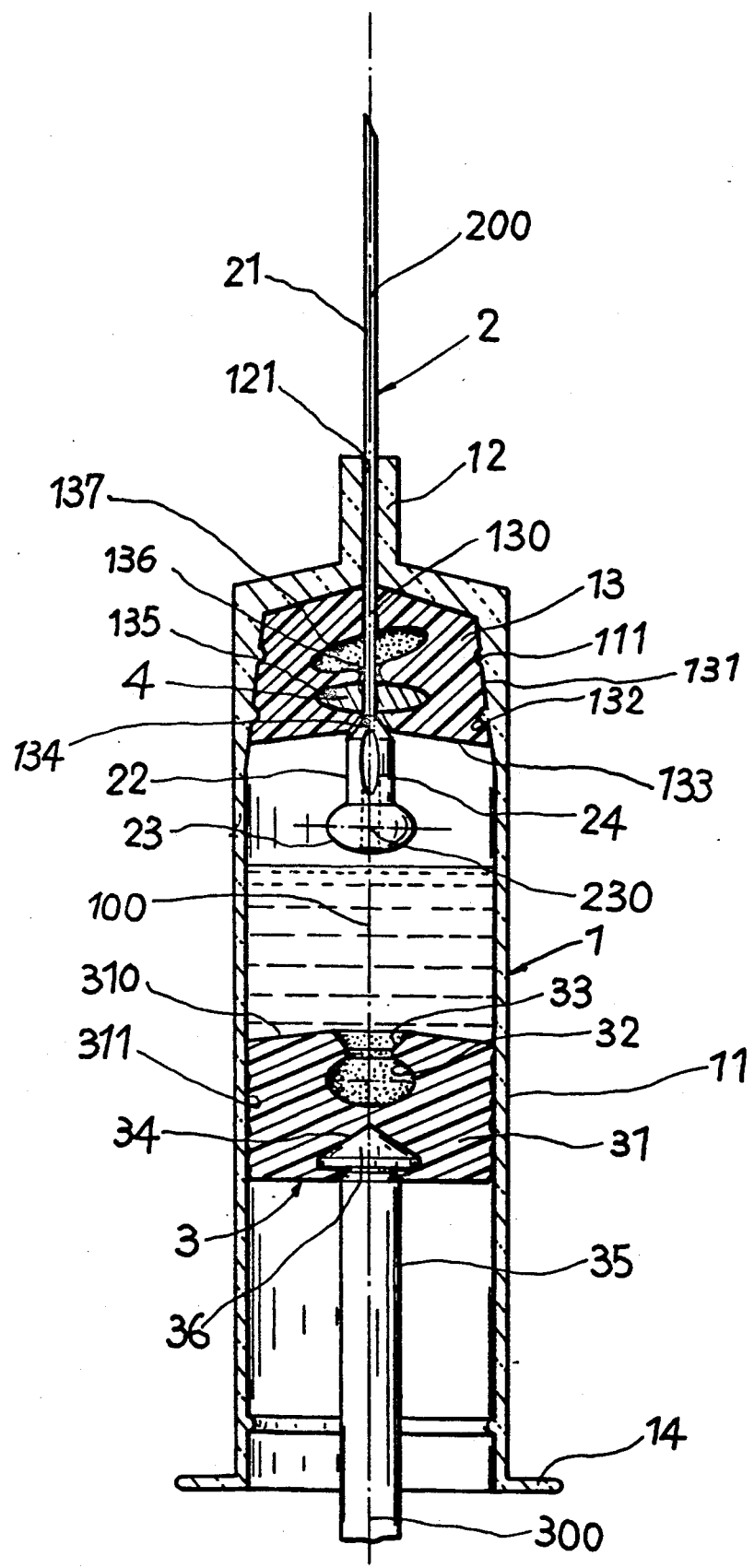
FIG. 1 is an illustration showing the present invention before injection.

As shown in the drawing figures, the present invention comprises: a syringe means 1, a hollow needle 2, a plunger means 3, and a rigid blocking member 4 movably held in the syringe means 1.

The syringe means 1 includes: a syringe cylinder 11 having a hollow bore portion 10 defined in the syringe cylinder 11 and a syringe axis 100 longitudinally existing in a central portion of the syringe cylinder 11 having a plurality of annular extension rings concentrically formed in an inner front cone portion inside the cylinder 11, a sleeve portion 12 protruded frontwardly from the syringe cylinder 11 having a sleeve hole 121 formed in the sleeve portion 12 for holding a needle portion 21 of the hollow needle 2 in the sleeve hole 121, a flexible plug 13 perferably made of soft, flexible elastomer materials inserted in the front portion inside the cylinder 11 having a central hole 130 for passing the needle portion 21 therethrough, a cone portion 131 having a plurality of annular grooves 132 concentrically formed on the cone portion 131 engageable with the extension rings 111 in the cylinder 11 for fixing the plug 13 in the cylinder 11, a first disk socket 135 perpendicularly formed in a rear portion of the plug 13 and communicating with a plug guiding port 134 tapered frontwardly from a plug rear surface 133, a collar portion 134a formed between the first disk socket 135 and the plug guiding port 134, and a second disk socket 137 normally inclinedly formed in a front portion of the plug 13 communicating with the first disk socket 135 through a throat portion 136 formed between the two disk sockets 135, 137, of which either disk socket 133 or 137 is operatively engageable with the rigid blocking member 4, and a syringe handle 14 formed on a rear end portion of the cylinder 11.

As shown in FIG. 3, the flexible plug 13 includes the first disk socket 135 having a longitudinal section generally elliptic shaped and having a first socket center 135c intersected by a first transverse axis 135a, and a first conjugate axis 135b which is normally aligned with the syringe axis 100, thereby orienting the first transverse axis 135a to be normally perpendicular to the syringe axis 100.

The second disk socket 137 has a longitudinal section generally elliptic shaped and having a second socket center 137c intersected by a second transverse axis 137a, and a second conjugate axis 137b which defines an acute angle A with the syringe axis 100 and is unaligned with the syringe axis 100, thereby normally orienting the second transverse axis 137a inclinedly in the plug 13.

The sockets 135, 137 and the blocking member 4 may be formed as an olive shape, oval shape, a shallow cylindrical shape, or other suitable shapes for a mutual compatible engagement between the blocking member 4 and either socket 135 or 137.

As shown in FIG. 3, the rigid blocking member 4 is made of rigid plastic or other rigid, hard materials insertable in either socket 135 or 137 in the soft flexible plug 13, and is preferably formed as a circular or cylindrical disk having a longitudinal section of elliptc shape engageable with either disk socket 135 or 137 in the plug 13, having a through hole 41 formed in a central portion through the blocking member 4 for passing the needle portion 21 of the hollow needle 2 therethrough, a conjugate disk axis 42 existing in a center line of the through hole 41 operatively aligned with the syringe axis 100 when perpendicularly held in the first disk socket 135 in the plug 13 when longitudinally retaining the hollow needle 2 in the plug 13 to align a needle axis 200 longitudinally existing in the needle 2 with the syringe axis 100 for injecting a liquid medicine filled in the bore portion of the syringe cylinder 11.

The rigid blocking member 4 as held on the needle portion 21 to be limited by the shank portion 22 of the needle is operatively thrusted from the first disk socket 135 into the second disk socket 137 through the throat portion 136 between the two disk sockets 135, 137, with the throat portion 136 defining a diameter (d) smaller than a length of the transverse axis 135a or 137a of any said disk socket 135, 137.

The hollow needle 2 includes: a needle portion 21 protruding outwardly through the sleeve hole 121 of the syringe means 1 having a tip end 211 formed on an outer end of the needle, a shank portion 22 connected with the needle portion 21 with a cone portion 221 tapered frontwardly towards the needle portion 21 to be normally engageably held in the blocking member 4 and in the collar portion 134a of the plug 13 for normal injection of the syringe means, a needle head portion 23 formed on a rear portion of the shank portion 22 normally protruding rearwardly beyond a plug rear surface 133 to be engageable with a needle-head socket 32 formed in the plunger means having an injection hole 231 formed in the needle head portion 23 communicating with a needle hole 20 formed through the hollow needle 2, a needle axis 200 longitudinally existing in a central portion of the needle 2 normally aligned with the syringe axis 100 when held in the plug 13 for normal injection purpose as shown in FIG. 1, and at least a venting slot 24 formed in the shank portion 22 adjacent to the needle head portion 23 for venting air outwardly through the needle hole 20 of the hollow needle.

The needle head portion 23 of the hollow needle 2 may be formed as elliptic shape to be engaged with an elliptical socket 32 formed in the plunger means 3, but not limited in this invention.

The plunger means 3 includes: a plunger 31 having a plurality of annular rings 311 circumferentially formed on the plunger reciprocatively held in the syringe cylinder 11, the needle head socket 32 recessed in a front end portion of the plunger 31 operatively engageable with the needle head portion 23 having a plunger guiding port 33 tapered rearwardly from a plunger front surface 310 for communicating with the needle-head socket 32 for engageably receiving and coupling the needle head portion 23 when finishing the injection for a retraction of the needle 2 as coupled to the plunger 31 into the syringe cylinder 11, a plunger rod 35 having a coupling member 36 engaged with a rear recess 34 formed in the plunger 31 for coupling the plunger 31 on the rod 35 and a plunger handle 37 for pushing the plunger 31 for boosting liquid medicine in the syringe cylinder 11 for injection use. The needle head socket 32 has a socket center aligned with a plunger axis 300 which is aligned with the syringe axis 100 and longitudinally formed in a center line of the plunger means, and projectively aligned with a needle head center 230 of the needle head portion 23 for a snug engagement of the needle head portion 23 with the needle-head socket 32 of the plunger 31 for coupling the needle 2 to the plunger means 3 which is operatively pushed frontwardly for movably driving the rigid blocking member 4 from a first disk socket 135 to a second disk socket 137 when finishing the injection (FIG. 5) and is then retracted to pull the needle coupled on the plunger to be stored into the syringe cylinder 11, whereby the rigid blocking member 4 will then be automatically restored by the flexible plug 13 to be inclinedly positioned in the plug 13 and the central through hole 41 of the blocking member 4 is then unaligned with the needle axis 200 and syringe axis 100 as shown in FIG. 6 for blocking an outward protrusion of the retracted needle portion 21 for preventing a sting injury or infectious contamination by the needle 2.

Figure 7:
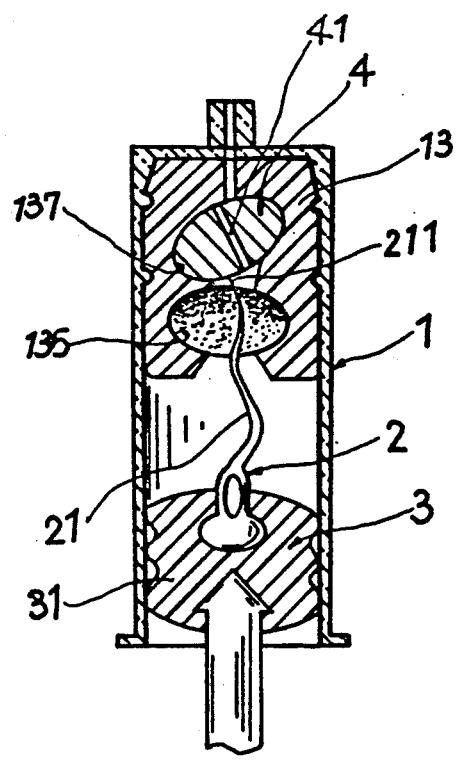
FIG. 7 shows a blocking effect for retarding an outwardly protruded needle in accordance with the present invention
Figure 8:
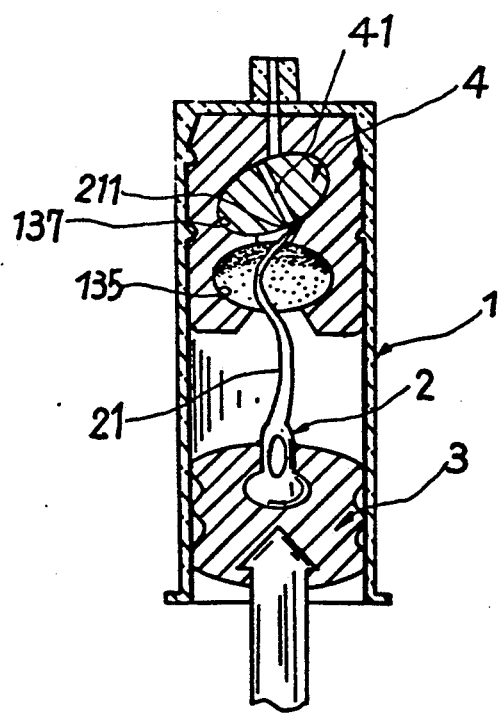
FIG. 8 shows another blocking effect of the present invention.

As shown in FIGS. 7 and 8, a further outward protrusion of the needle 2 will be automatically blocked by the blocking member 4 by bending or deforming the needle tip end 211 which can not be pushed outwardly from the syringe cylinder 11 for a better safety and hygienic protection.

Figure 5:
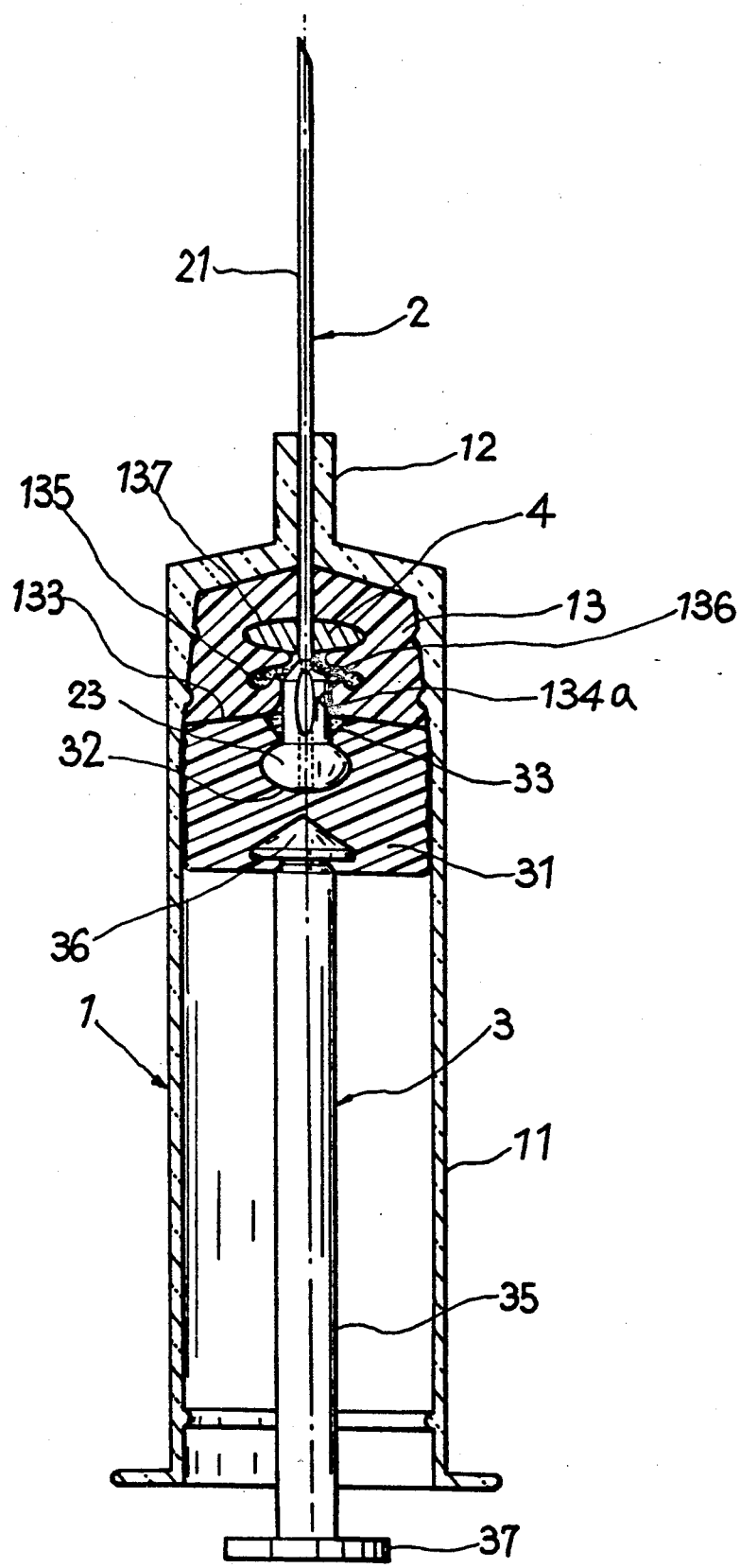
FIG. 5 is an illustration showing the present invention when finishing the injection.
Figure 6:
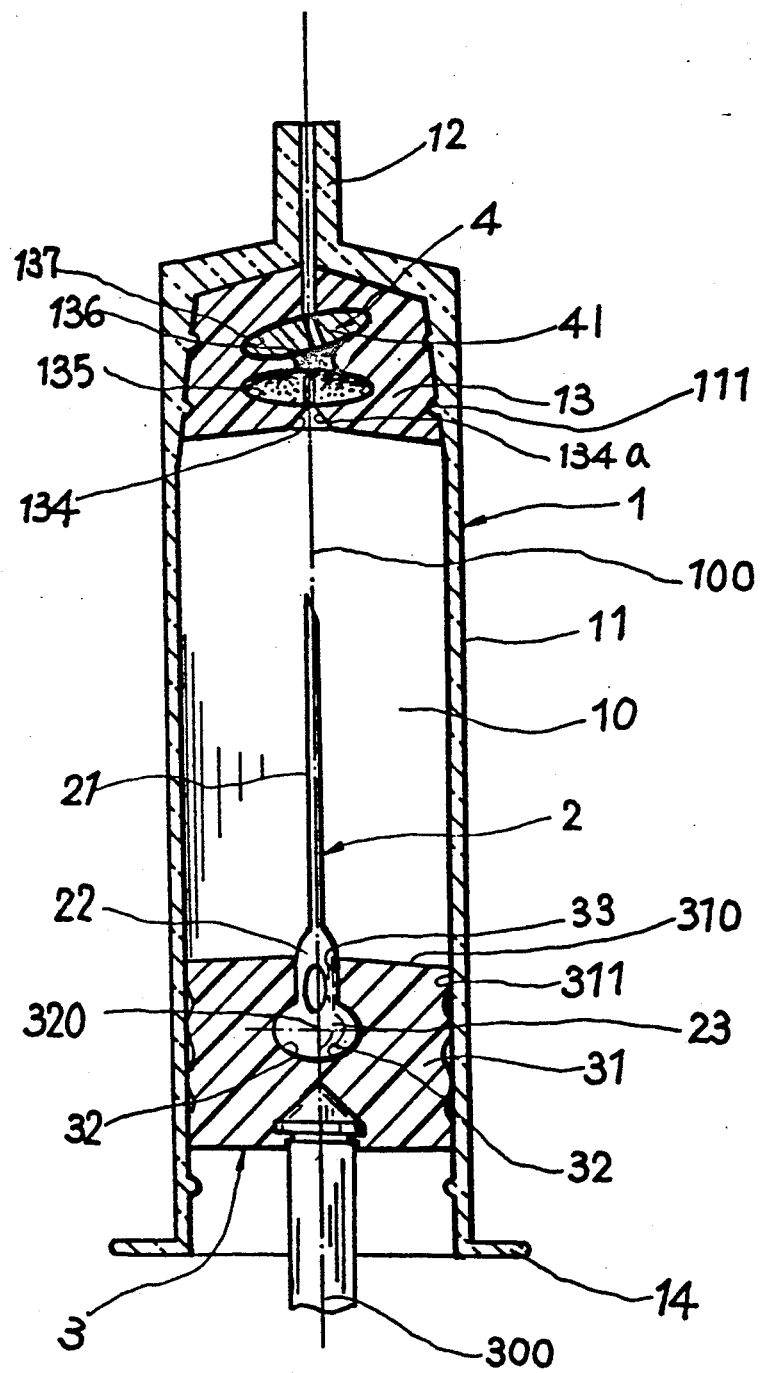
FIG. 6 shows a retracted needle in the syringe of the present invention.

After the retraction of the needle 2 coupled to the plunger 31 into the syringe cylinder 11 as shown in FIG. 6, the flexible plug 13 will be automatically restored by its self elasticity to restore the second socket 137, from its flattened state (blocking member 4 perpendicular to the axis 100) as pressurized by the plunger means 3 as shown in FIG. 5, to be an inclined situation wherein the rigid hard blocking member 4 will be restored to be inclinedly positioned (FIG. 6), thereby blocking the unexpected outwardly protrusion of a retracted needle 2 especially as shown in FIGS. 7, 8.

I claim:

1. A safety syringe comprising:
   a syringe means having a flexible plug inserted in a front portion inside a syringe cylinder of said syringe means, said flexible plug having a first disk socket formed in a rear portion in said plug normally perpendicular to a syringe axis longitudinally existing in a central portion of said syringe cylinder, and a second disk socket formed in a front portion in said plug and communicating with said first socket and normally inclinedly positioned in said plug; and
   a rigid blocking member having a central through hole normally engageable held in the first disk socket of said plug; and a hollow needle normally held in said blocking member and in said plug, and operatively thrusted frontwardly as urged by a plunger means reciprocatively held in said syringe means to be transferred into said second disk socket when finishing an injection, said needle being operatively coupled to said plunger means when finishing the injection, whereby upon a retraction of said needle into said syringe cylinder, said plug will automatically restore said second disk socket to inclinedly orient said rigid block member to unalign the through hole of said blocking member with said needle, thereby preventing an outward protrusion of the needle from said syringe cylinder.

2. A safety syringe according to claim 1, wherein said syringe means includes: the syringe cylinder having a hollow bore portion defined in the syringe cylinder and a syringe axis longitudinally existing in a central portion of the syringe cylinder having a plurality of annular extension rings concentrically formed in an inner front cone portion inside the cylinder, a sleeve portion protruded frontwardly from the syringe cylinder having a sleeve hole formed in the sleeve portion for holding a needle portion of the hollow needle in the sleeve hole, the flexible plug inserted in the front portion inside the cylinder having a central hole for passing the needle portion therethrough, a cone portion having a plurality of annular grooves concentrically formed on the cone portion engageable with the extension rings in the cylinder for fixing the plug in the cylinder, the first disk socket perpendicularly formed in a rear portion of the plug and communicating with a plug guiding port tapered frontwardly from a plug rear surface, a collar portion formed between the first disk socket and the plug guiding port, and a second disk socket normally inclinedly formed in a front portion of the plug communicating with the first disk socket through a throat portion formed between the two disk sockets, of which any said disk socket is operatively engageable with the rigid blocking member, and a syringe handle formed on a rear end portion of the cylinder.

3. A safety syringe according to claim 2, wherein said flexible plug includes the first disk socket having a longitudinal section generally elliptic shaped and having a first socket center intersected by a first transverse axis, and a first conjugate axis which is normally aligned with the syringe axis, thereby orienting the first transverse axis to be normally perpendicular to the syringe axis.

4. A safety syringe according to claim 2, wherein said second disk socket has a longitudinal section generally elliptic shaped and having a second socket center intersected by a second transverse axis, and a second conjugate axis which defines an acute angle with the syringe axis and is unaligned with the syringe axis, thereby normally orienting the second transverse axis inclinedly in the plug.

5. A safety syringe according to claim 2, wherein said rigid blocking member is made of rigid materials insertable in any said socket in the flexible plug, and is formed as a circular disk having a longitudinal section of elliptc shape engageable with any said disk socket in the plug, having the through hole formed in a central portion through the blocking member for passing the needle portion of the hollow needle therethrough, a conjugate disk axis existing in the center line of the through hole operatively aligned with the syringe axis when perpendicularly held in the first disk socket in the plug when longitudinally retaining the hollow needle in the plug to align a needle axis longitudinally existing in the needle with the syringe axis for injecting a liquid medicine filled in the bore portion of the syringe cylinder outwardly.

6. A safety syringe according to claim 5, wherein said rigid blocking member as held on the needle portion to be limited by the shank portion of the needle is operatively thrusted from the first disk socket into the second disk socket through the throat portion between the two disk sockets, with the throat portion defining a diameter smaller than a length of the transverse axis of any said disk socket.

7. A safety syringe according to claim 2, wherein said hollow needle includes: the needle portion protruding outwardly through the sleeve hole of the syringe means having a tip end formed on an outer end of the needle, a shank portion connected with the needle portion with a cone portion tapered frontwardly towards the needle portion to be normally engageably held in the blocking member and in the collar portion of the plug for normal injection of the syringe means, a needle head portion formed on a rear portion of the shank portion normally protruding rearwardly beyond a plug rear surface to be engageable with a needle-head socket formed in the plunger means having an injection hole formed in the needle head portion communicating with a needle hole formed through the hollow needle, a needle axis longitudinally existing in a central portion of the needle normally aligned with the syringe axis when held in the plug for normal injection purpose, and at least a venting slot formed in the shank portion adjacent to the needle head portion for venting air outwardly through the needle hole of the hollow needle.

8. A safety syringe according to claim 7, wherein said plunger means includes: a plunger having a plurality of annular rings circumferentially formed on the plunger reciprocatively held in the syringe cylinder, the needle head socket recessed in a front end portion of the plunger operatively engageable with the needle head portion having a plunger guiding port tapered rearwardly from a plunger front surface for communicating with the needle-head socket for engageably receiving and coupling the needle head portion when finishing the injection for a retraction of the needle as coupled to the plunger into the syringe cylinder, a plunger rod having a coupling member engaged with a rear recess formed in the plunger for coupling the plunger on the rod and a plunger handle for pushing the plunger for boosting liquid medicine in the syringe cylinder for injection use; said needle head socket having a socket center aligned with a plunger axis which is aligned with the syringe axis and longitudinally formed in a center line of the plunger means, and projectively aligned with a needle head center of the needle head portion of said needle for a snug engagement of the needle head portion with the needle-head socket of the plunger for coupling the needle to the plunger means.

* * * * *